(12) United States Patent
Kondo et al.

(10) Patent No.: US 11,610,575 B2
(45) Date of Patent: Mar. 21, 2023

(54) ULTRASONIC ENDOSCOPE ACOUSTIC LENS AND ULTRASONIC ENDOSCOPE

(71) Applicant: OLYMPUS CORPORATION, Hachioji (JP)

(72) Inventors: Takayuki Kondo, Tokyo (JP); Koji Kobayashi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 947 days.

(21) Appl. No.: 16/442,919

(22) Filed: Jun. 17, 2019

(65) Prior Publication Data

US 2019/0298306 A1    Oct. 3, 2019

Related U.S. Application Data

(63) Continuation of application No. PCT/JP2017/043799, filed on Dec. 6, 2017.

(30) Foreign Application Priority Data

Dec. 22, 2016  (JP) .................. 2016-249482

(51) Int. Cl.

| G10K 11/30 | (2006.01) |
| C08L 83/04 | (2006.01) |
| A61B 8/12 | (2006.01) |
| B06B 1/06 | (2006.01) |
| C08K 3/08 | (2006.01) |

(52) U.S. Cl.
CPC .............. *G10K 11/30* (2013.01); *C08L 83/04* (2013.01); *A61B 8/12* (2013.01); *B06B 1/067* (2013.01); *C08K 2003/0812* (2013.01); *C08K 2201/005* (2013.01)

(58) Field of Classification Search
None
See application file for complete search history.

(56) References Cited

U.S. PATENT DOCUMENTS

| 2005/0070801 A1* | 3/2005 | Yamashita ............ A61B 8/4281 600/459 |
| 2007/0063616 A1* | 3/2007 | Adachi ................ A61B 8/4483 310/311 |
| 2008/0098816 A1* | 5/2008 | Yamashita ............ B06B 1/0629 310/335 |

FOREIGN PATENT DOCUMENTS

| CN | 101172044 A | 5/2008 |
| EP | 1862227 A2 | 12/2007 |
| JP | 62011897 A | 1/1987 |
| JP | 08305375 A | 11/1996 |
| JP | 2598829 B2 * | 4/1997 |
| JP | 2005125071 A | 5/2005 |
| JP | 2005340903 A | 12/2005 |
| JP | 2008011494 A | 1/2008 |

OTHER PUBLICATIONS

ACS Appl Mater Interfaces Mishra 7-14303-14316 (2025).*
JP-2598829-B2 English machine Translation (1997).*
(Continued)

*Primary Examiner* — Kenneth J Stachel
(74) *Attorney, Agent, or Firm* — Holtz, Holtz & Volek PC (57) ABSTRACT

An acoustic lens contains a base material composed of a diorganopolysiloxane or a silicone rubber compound utilizing a diorganopolysiloxane as a main component, and plate-like inorganic compound particles dispersed in the base material.

6 Claims, 6 Drawing Sheets

(56) References Cited

OTHER PUBLICATIONS

International Search Report (ISR) (and English language translation thereof) dated Mar. 13, 2018 issued in counterpart International Application No. PCT/JP2017/043799.

Chinese Office Action (and English language translation thereof) dated Apr. 8, 2021 issued in Chinese Application No. 201780069008.5.

* cited by examiner

ULTRASONIC ENDOSCOPE ACOUSTIC LENS AND ULTRASONIC ENDOSCOPE

The application is a continuation application based on a PCT Patent Application No. PCT/JP2017/043799, filed Dec. 6, 2017, whose priority is claimed on Japanese Patent Application No. 2016-249482, filed Dec. 22, 2016. The content of both the PCT Application and the Japanese Application are incorporated herein by reference.

BACKGROUND OF THE INVENTION

Field of the Invention

The present invention relates to an ultrasonic endoscope acoustic lens and an ultrasonic endoscope.

Description of Related Art

Ultrasonic endoscopes are known as medical endoscopes.

Ultrasonic endoscopes are equipped with an ultrasonic transducer for acquiring an image of a subject. An acoustic lens for converging ultrasonic waves is disposed on a surface of the ultrasonic transducer.

The acoustic lens is required to have an acoustic impedance close to a subject, such as biological tissue, so as to introduce ultrasonic waves efficiently into the subject. When the acoustic impedance of the acoustic lens is close to the acoustic impedance of a biological tissue, surface reflection is decreased at a portion in contact with the biological tissue, and thus ultrasonic waves are efficiently propagated to the biological tissue.

For example, a composition for an acoustic lens used in a probe for a medical ultrasonic diagnostic device is disclosed in Japanese Unexamined Patent Application, First Publication No. S62-11897. In the composition for an acoustic lens, an aluminum or titanium oxide powder having an average particle size of 0.1 to 1.0 µm, and a thermoplastic resin powder having an average particle size of 0.1 to 50 µm and a melting point of 80° C. or higher are included with a diorganopolysiloxane or a silicone rubber compound utilizing a diorganopolysiloxane as a main component.

SUMMARY OF THE INVENTION

An ultrasonic endoscope acoustic lens of a first aspect of the present invention contains a base material composed of a diorganopolysiloxane or a silicone rubber compound utilizing a diorganopolysiloxane as a main component, and plate-like inorganic compound particles dispersed in the base material.

According to an ultrasonic endoscope acoustic lens of a second aspect of the present invention, an average particle size of the inorganic compound particles in a surface direction may be 10 nm or more and 30 µm or less.

According to an ultrasonic endoscope acoustic lens of a third aspect of the present invention, an aspect ratio of the inorganic compound particles which is a ratio of an average particle size in a surface direction to a thickness may be 2 or more and 2000 or less.

According to an ultrasonic endoscope acoustic lens of a fourth aspect of the present invention, the inorganic compound particles may contain one or more selected materials from the group consisting of alumina, silica, boehmite, cerium oxide, titanium oxide, magnesium oxide, zinc oxide, boron nitride, aluminum nitride, and aluminum hydroxide.

According to an ultrasonic endoscope acoustic lens of a fifth aspect of the present invention, the inorganic compound particles may be orientated in a direction along a surface of the acoustic lens.

According to an ultrasonic endoscope acoustic lens of a sixth aspect of the present invention, gradients of the inorganic compound particles with respect to the surface may be 0° or more and 45° or less.

According to an endoscope acoustic lens of a seventh aspect of the present invention, 1 part by mass or more and 100 parts by mass or less of the inorganic compound particles may be included with respect to 100 parts by mass of the base material.

An ultrasonic endoscope of an eighth aspect of the present invention includes the ultrasonic endoscope acoustic lens.

DETAILED DESCRIPTION OF THE INVENTION

Hereinafter, embodiments of the present invention will be described with reference to the drawings. In all the drawings, even in a case where the embodiments are different, identical or equivalent members are given the same reference signs, and common descriptions are omitted.

First Embodiment

Hereinafter, an ultrasonic endoscope acoustic lens of a first embodiment of the present invention will be described.

Figure 1:
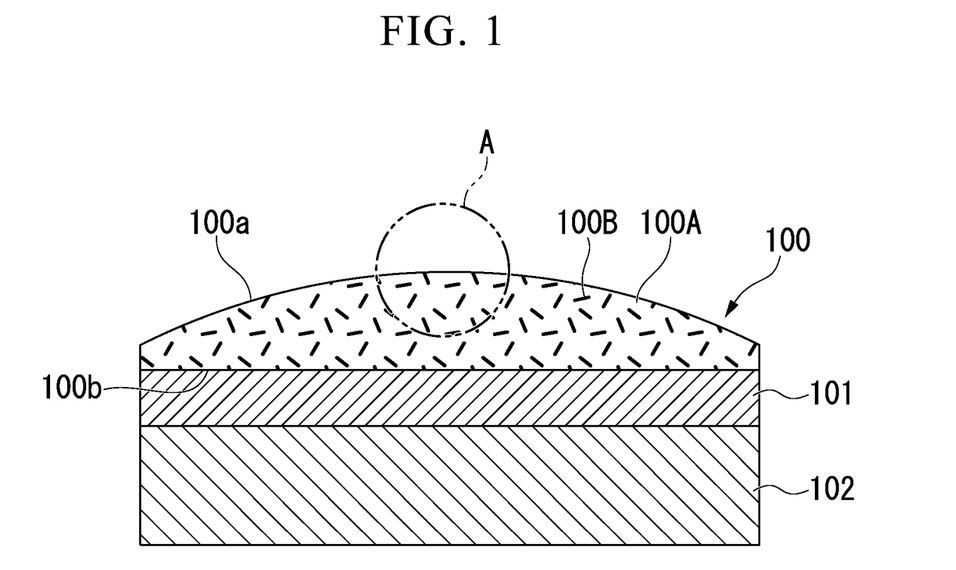
FIG. 1 is a schematic sectional view showing an example of an ultrasonic endoscope acoustic lens of a first embodiment of the present invention.
Figure 2A:
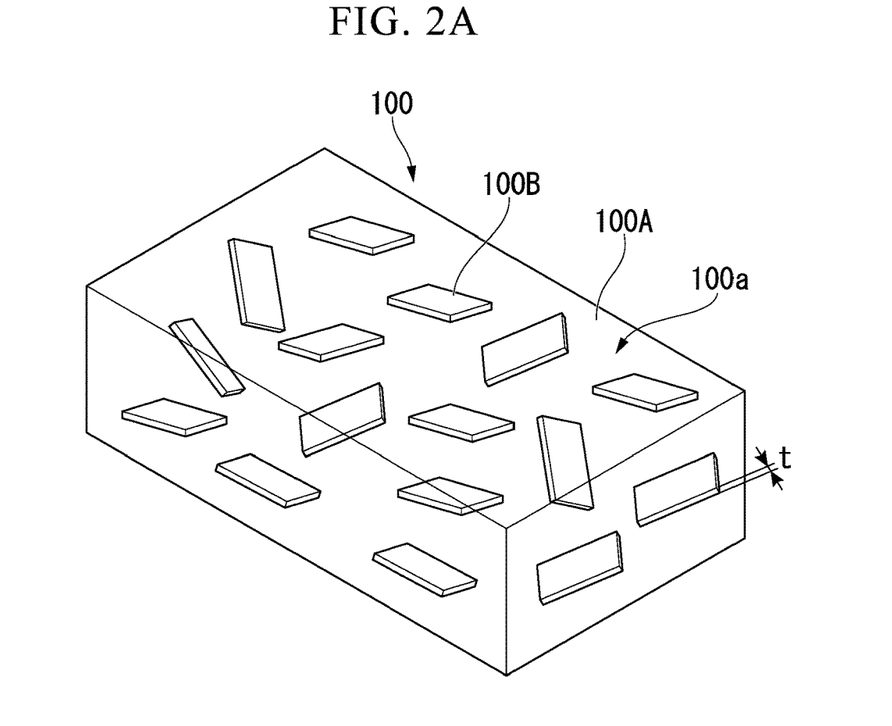
FIG. 2A is a schematic perspective view showing an internal constitution of part A in FIG. 1.
Figure 2B:
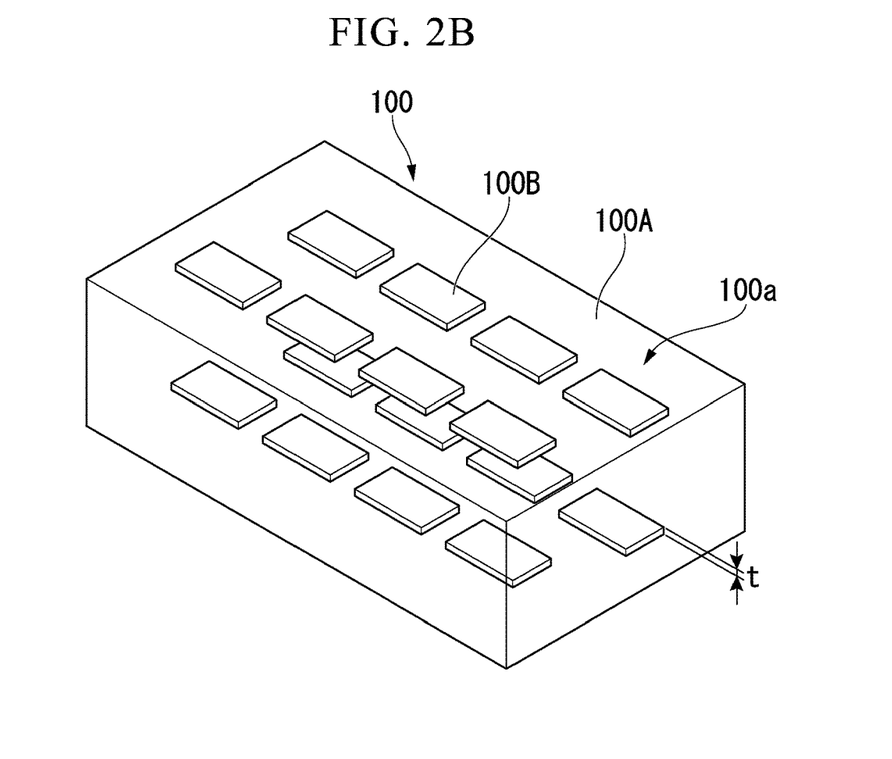
FIG. 2B is a schematic perspective view showing the internal constitution of the part A in FIG. 1.

FIG. 1 is a schematic sectional view showing an example of an ultrasonic endoscope acoustic lens of a first embodiment of the present invention. FIGS. 2A and 2B are schematic perspective views showing an internal constitution of part A in FIG. 1.

As shown in FIG. 1, an acoustic lens 100 of the present embodiment (an ultrasonic endoscope acoustic lens) includes base material 100A and plate-like inorganic compound particles 100B.

The acoustic lens 100 may be suitably used in an ultrasonic transducer of a medical ultrasonic endoscope.

The acoustic lens 100 is fixed to a surface of a piezoelectric element 102 that generates ultrasonic vibration via an acoustic matching layer 101 in order to constitute an ultrasonic transducer.

The acoustic matching layer 101 is a layered part that reduces a difference in acoustic impedance between a subject and the piezoelectric element 102. Depending on the acoustic impedance of the subject, the acoustic impedance of the acoustic matching layer 101 is suitably set, and thus reflection of ultrasonic waves from the subject is reduced.

A section of the acoustic lens 100 is formed in such a suitable shape with which ultrasonic waves generated by the piezoelectric element 102 are converged toward the subject. In the example shown in FIG. 1, a junction surface 100b of the acoustic lens 100 joined to the acoustic matching layer 101 is flat. A lens surface 100a of the acoustic lens 100 is a curved surface that bulges outward. The lens surface 100a is formed by a surface of the base material 100A except that the plate-like inorganic compound particles 100B are exposed in a part thereof.

The base material 100A includes a diorganopolysiloxane or a silicone rubber compound utilizing a diorganopolysiloxane as a main component. A structure of the diorganopolysiloxane or the composition of the silicone rubber compound utilizing a diorganopolysiloxane as a main component, which is used in the base material 100A, is not particularly limited. As a structure of an organic group in the diorganopolysiloxane and the composition of the silicone rubber compound utilizing a diorganopolysiloxane as a main component, any of the structures disclosed, for example, in Japanese Unexamined Patent Application, First Publication No. S62-11897 may be used.

The plate-like inorganic compound particles 100B are inorganic compound particles with a plate shape. Acoustic characteristics required for the acoustic lens 100 are obtained by adding the plate-like inorganic compound particles 100B to the base material 100A in an adequate amount. The plate-like inorganic compound particles 100B are dispersed in the base material 100A.

The term "plate shape" used herein refers to, especially a flat shape in one direction. For example, when three of various orthogonal axes of the particle are used to measure external dimensions in direction of the axes, a direction in which the minimum dimension is obtained is referred to as "thickness direction." The term "plate shape" may be defined as a shape in which an average external dimension in the directions of two arbitrary axes perpendicular to the thickness direction is greater than the external dimension in the "thickness direction."

The external dimension in the "thickness direction" of the "plate-like" particle may or may not be constant in the direction perpendicular to the "thickness direction." The maximum value of the external dimension in the "thickness direction" is referred to as "thickness." Hereinafter, a surface spreading in the direction perpendicular to the "thickness direction" is referred to as "plate surface," and the direction perpendicular to the "thickness direction" is referred to as "surface direction." In this case, the term "plate shape" may also be said to be a shape in which an average outer dimension in the "surface direction" is greater than that in the "thickness direction."

The shapes of the plate-like inorganic compound particles 100B when viewed in the thickness direction may be, for example, polygonal shapes.

An average particle size of the plate-like inorganic compound particles 100B in the surface direction (a surface-direction average particle size) may be 10 nm to 30 μm. In this case, the strength of the plate-like inorganic compound particles 100B with respect to physical impact and the acoustic characteristics of the acoustic lens 100 become superior.

Here, the surface-direction average particle size is a numerical value obtained by averaging outer diameters viewed in the thickness direction in a sample group.

The outer diameter of each particle viewed in the thickness direction is defined, for example, by the maximum width in the surface direction (the direction perpendicular to the thickness direction) in an outline observed in the thickness direction using a scanning electron microscope.

When the surface-direction average particle size is less than 10 nm, the plate-like inorganic compound particles 100B readily become clumped, so that it may be difficult to disperse the plate-like inorganic compound particles 100B in the base material 100A. When the plate-like inorganic compound particles 100B are clumped, it may also be difficult to control an orientation of the plate-like inorganic compound particles 100B in the base material 100A.

When the surface-direction average particle size exceeds 30 μm, an attenuation factor of sound waves becomes too high, so that there is a chance of acoustic performance being deteriorated in view of the attenuation factor.

The ratio of the surface-direction average particle size to the thickness of the plate-like inorganic compound particle 100B (the surface-direction average particle size/the thickness) is defined as an aspect ratio of the plate-like inorganic compound particle 100B.

The aspect ratio of the plate-like inorganic compound particle 100B may be 2 or more and 2000 or less.

When the aspect ratio is less than 2, the shapes of the plate-like inorganic compound particles 100B are close to granular bodies that are not so flat, and thus the mechanical strength of the acoustic lens 100 may not be much improved.

When the aspect ratio exceeds 2000, the plate-like inorganic compound particles 100B are easily broken when the acoustic lens 100 is formed, and thus variation in acoustic characteristics or mechanical strength may increase.

The plate-like inorganic compound particles 100B are more preferably formed of a material that provides a high density. In this case, even if an amount of the plate-like inorganic compound particles 100B is small, suitable acoustic characteristics of the acoustic lens 100 are readily obtained. When the amount of the plate-like inorganic compound particles 100B is small, fluidity of a composition in which the plate-like inorganic compound particles 100B are mixed with the base material 100A before curing can be improved. For this reason, moldability of the acoustic lens 100 is improved. As a result, since a shape of a molding die when the acoustic lens 100 is molded can be accurately transferred to the acoustic lens 100, lens characteristics such as focusability in the acoustic lens 100 is improved.

Furthermore, since a high-density material also generally has great mechanical strength, the mechanical strength of the acoustic lens 100 is easily increased.

From these viewpoints, the plate-like inorganic compound particles 100B may, for example, include one or more materials selected from the group consisting of alumina, silica, boehmite, cerium oxide, titanium oxide, magnesium oxide, zinc oxide, boron nitride, aluminum nitride, and aluminum hydroxide.

The materials provided as exemplary examples of the particles here have higher density and stronger mechanical strength than the base material 100A. For this reason, by adding at least one or more of these materials to the base material 100A, the acoustic characteristics of the acoustic lens 100 can be adequately adjusted, and the mechanical strength of the acoustic lens 100 can be improved.

Alumina is particularly preferable because it is readily formed into a plate-like shape, and a density and mechanical strength of the plate-like body are also excellent.

The amount of the plate-like inorganic compound particles 100B in the acoustic lens 100 may be set as an adequate content by which the acoustic characteristics and the mechanical strength required for the acoustic lens 100 are obtained.

For example, the amount of the plate-like inorganic compound particles 100B in the acoustic lens 100 may be 1 part by mass or more and 100 parts by mass or less with respect to 100 parts by mass of the base material 100A.

When there is less than 1 part by mass of the plate-like inorganic compound particles 100B, since an amount of the plate-like inorganic compound particles 100B added is small, it may be difficult to adequately adjust the acoustic impedance of the acoustic lens 100, and the mechanical strength of the acoustic lens 100 may not be able to be much improved.

When the amount of the plate-like inorganic compound particles 100B exceeds 100 parts by mass, the moldability of the acoustic lens 100 is deteriorated, and thus the mechanical strength of the acoustic lens 100 may not be able to be much improved. Furthermore, when the added amount of the plate-like inorganic compound particles 100B is increased, the attenuation factor of sound waves may be increased.

The acoustic lens 100 having this constitution is manufactured by kneading the base material 100A and the plate-like inorganic compound particles 100B and molding and vulcanizing it into a shape of the acoustic lens 100, for example, by pressing or the like.

Since the plate-like inorganic compound particles 100B have plate-like shapes, the plate-like inorganic compound particles 100B flows easily along a molding die in a molding process. For this reason, in attitudes of the plate-like inorganic compound particles 100B, the surface direction is readily orientated in a flowing direction.

For example, FIG. 2A schematically shows an example of an internal structure adjacent to the lens surface 100a. A radius of curvature of the lens surface 100a is significantly larger than the surface-direction average particle size of the plate-like inorganic compound particles 100B. For this reason, the lens surface 100a facing the plate-like inorganic compound particles 100B is approximately regarded as the same plane as a tangential plane of the lens surface 100a.

In FIGS. 2A and 2B, as an example of the shape of each plate-like inorganic compound particle 100B, a rectangular plate-like shape having a thickness t is drawn. However, each plate-like inorganic compound particle 100B may have a plate-like shape other than a rectangular plate-like shape.

In the example schematically shown in FIG. 2A, the attitudes of the plate-like inorganic compound particles 100B vary around an attitude parallel to the lens surface 100a. This is because a state where the surface directions of the plate-like inorganic compound particles 100B are coincident with the flowing direction in the molding process is a state where resistance is lowest.

In the example schematically shown in FIG. 2B, the plate-like inorganic compound particles 100B are orientated parallel to the lens surface 100a. An orientation state close to this state is particularly easily obtained in a case where roll pressing is performed in the molding process.

When the plate-like inorganic compound particles 100B in the acoustic lens 100 are orientated approximately parallel to the lens surface 100a in the vicinity of at least the lens surface 100a, an arrangement density of the plate-like inorganic compound particles 100B when viewed in a normal direction of the lens surface 100a increases. For this reason, the mechanical strength of the acoustic lens 100 against an external force applied in a direction around the normal direction of the lens surface 100a is improved.

Furthermore, since rigidity in a direction parallel to the lens surface 100a increases, durability against bending deformation or a frictional force on the lens surface 100a is improved.

To improve the mechanical strength of the acoustic lens 100, and particularly mechanical strength for reducing damage on the lens surface 100a, the plate-like inorganic compound particles 100B are more preferably orientated in the direction along the lens surface 100a. The plate-like inorganic compound particles 100B are also more preferably orientated in the direction approximately or averagely parallel to the lens surface 100a. The plate-like inorganic compound particles 100B are much preferably orientated in the direction parallel to the lens surface 100a.

In the case where the plate-like inorganic compound particles 100B are orientated in the direction along the lens surface 100a, gradients of the plate-like inorganic compound particles 100B with respect to the lens surface 100a may be 0° or more and 45° or less. A proportion of the plate-like inorganic compound particles 100B whose gradients with respect to the lens surface 100a are 0° or more and 45° or less is more preferably higher than or equal to 49%.

However, since it may be difficult to know exact gradients of the numerous plate-like inorganic compound particles 100B in an actual product, the exact gradients are determined by a measuring method (to be described below).

Figure 3:
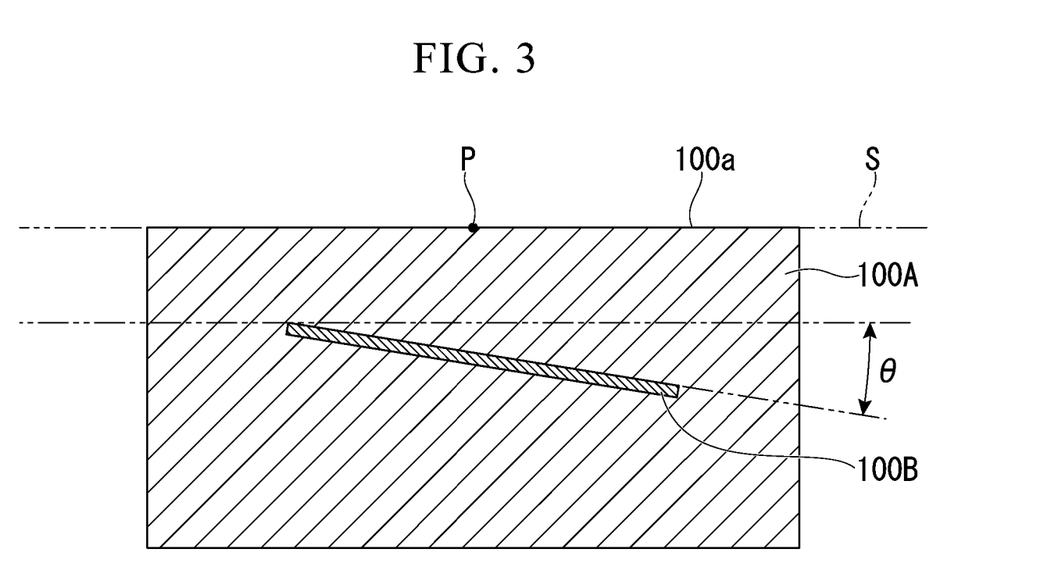
FIG. 3 is a schematic view showing a method of measuring a gradient of an inorganic compound particle having a plate-like shape.

First, a measurement sample in which first and second sections including the normal to the lens surface 100a and perpendicular to each other are exposed is produced. The sections of the measurement sample (the first and second sections) are observed by an electron microscope, and thus gradients of the plate-like inorganic compound particles 100B in the sections are measured on the basis of the observed image. As shown in FIG. 3, a gradient θ (where θ is 0° or more and 90° or less) of a specified plate-like inorganic compound particle 100B with respect to the lens surface 100a is measured with respect to a tangential plane S that passes through a point P on the lens surface 100a facing the plate-like inorganic compound particle 100B. However, in a case where an observation area where a curvature of the lens surface 100a is sufficiently small is selected, one common plane in each observation area may be used for the tangential plane S serving as a measurement reference.

Next, a distribution of the gradients θ in the first and second sections is required. For example, a proportion at which the gradient in the first section becomes θ1 to θ2 is set to x %, and a proportion at which the gradient in the second section becomes θ1 to θ2 is set to y %.

In a case of $x/100 \geq \sqrt{(z/100)}$ and $y/100 \geq \sqrt{(z/100)}$, it is determined that a proportion at which the gradient of each plate-like inorganic compound particle 100B with respect to the lens surface 100a is within a range of θ1 to θ2 is greater than or equal to z %.

For example, in a case where the rates at which the gradients in the first and second sections are 0° or more and 45° or less are more than or equal to 70%, it is determined that the proportion at which the gradients of the plate-like inorganic compound particles 100B with respect to the lens surface 100a are 0° or more and 45° or less is more than or equal to 49%.

Next, an action of the acoustic lens 100 will be described.

Since the acoustic lens 100 contains the plate-like inorganic compound particles 100B in the base material 100A, acoustic characteristics suitable for the acoustic lens of the ultrasonic endoscope are obtained by adequately setting the amount of the plate-like inorganic compound particles 100B.

The acoustic impedance is obtained as the product of a density of the medium and the speed of sound in the medium. The acoustic impedance needs to be set to an appropriate value depending on a subject. For example, since the plate-like inorganic compound particles 100B have a different density from that of the base material 100A, the acoustic impedance may be adjusted by changing the amount of the plate-like inorganic compound particles 100B with respect to the base material 100A. In a case where the density of the plate-like inorganic compound particles 100B is higher than that of the base material 100A, the acoustic impedance can be increased to higher than in a case of the base material 100A alone by increasing the amount of the plate-like inorganic compound particles 100B.

Furthermore, since the plate-like inorganic compound particles 100B have plate shape, refraction and scattering are less likely to occur in the plate-like inorganic compound particles in comparison with spherical inorganic compound particles formed of the same material. For this reason, it is less likely to increase the attenuation factor of sound waves in the acoustic lens 100.

Since the acoustic lens 100 contains an adequate amount of plate-like inorganic compound particles 100B, excellent mechanical strength is obtained.

For example, since the plate-like inorganic compound particles 100B are readily orientated in a direction along the lens surface 100a, rigidity of the acoustic lens 100 in the direction along the lens surface 100a is improved. For this reason, damage to the acoustic lens 100 from the lens surface 100a due to friction or the like acting on the lens surface 100a is suppressed.

For example, since an external force applied in a normal direction of the lens surface 100a is applied to flat surfaces of the plate-like inorganic compound particles 100B, mechanical strength of the acoustic lens 100 against the external force applied in the normal direction of the lens surface 100a is improved. For example, tolerance of the acoustic lens 100 to physical impact or the like applied in the normal direction lens surface 100a is improved.

As described above, the acoustic lens 100 of the present embodiment has excellent acoustic characteristics, and can improve durability against physical contact.

Second Embodiment

Next, an ultrasonic endoscope acoustic lens and an ultrasonic endoscope of a second embodiment of the present invention will be described.

Figure 4:
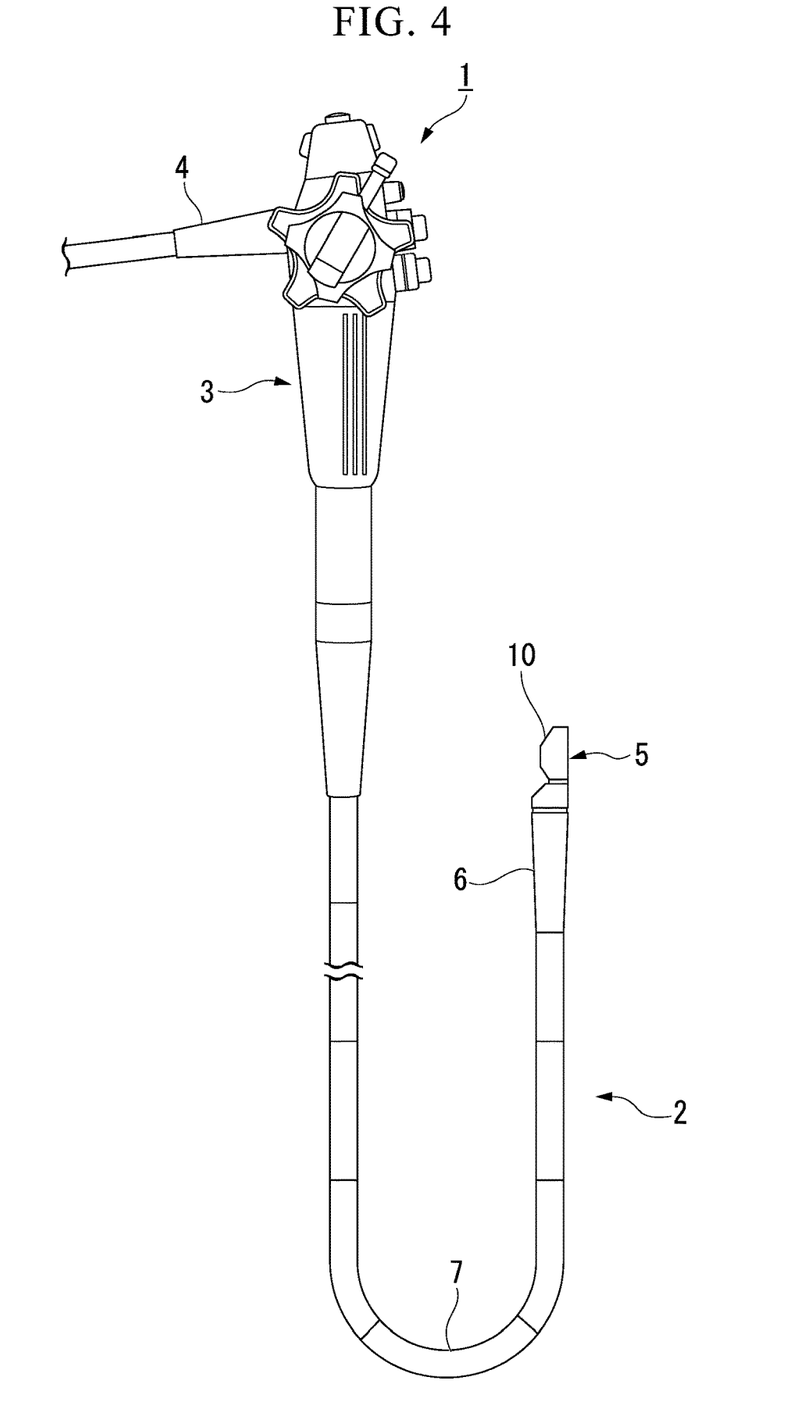
FIG. 4 is a schematic front view showing a general constitution of an ultrasonic endoscope of a second embodiment of the present invention.
Figure 5:
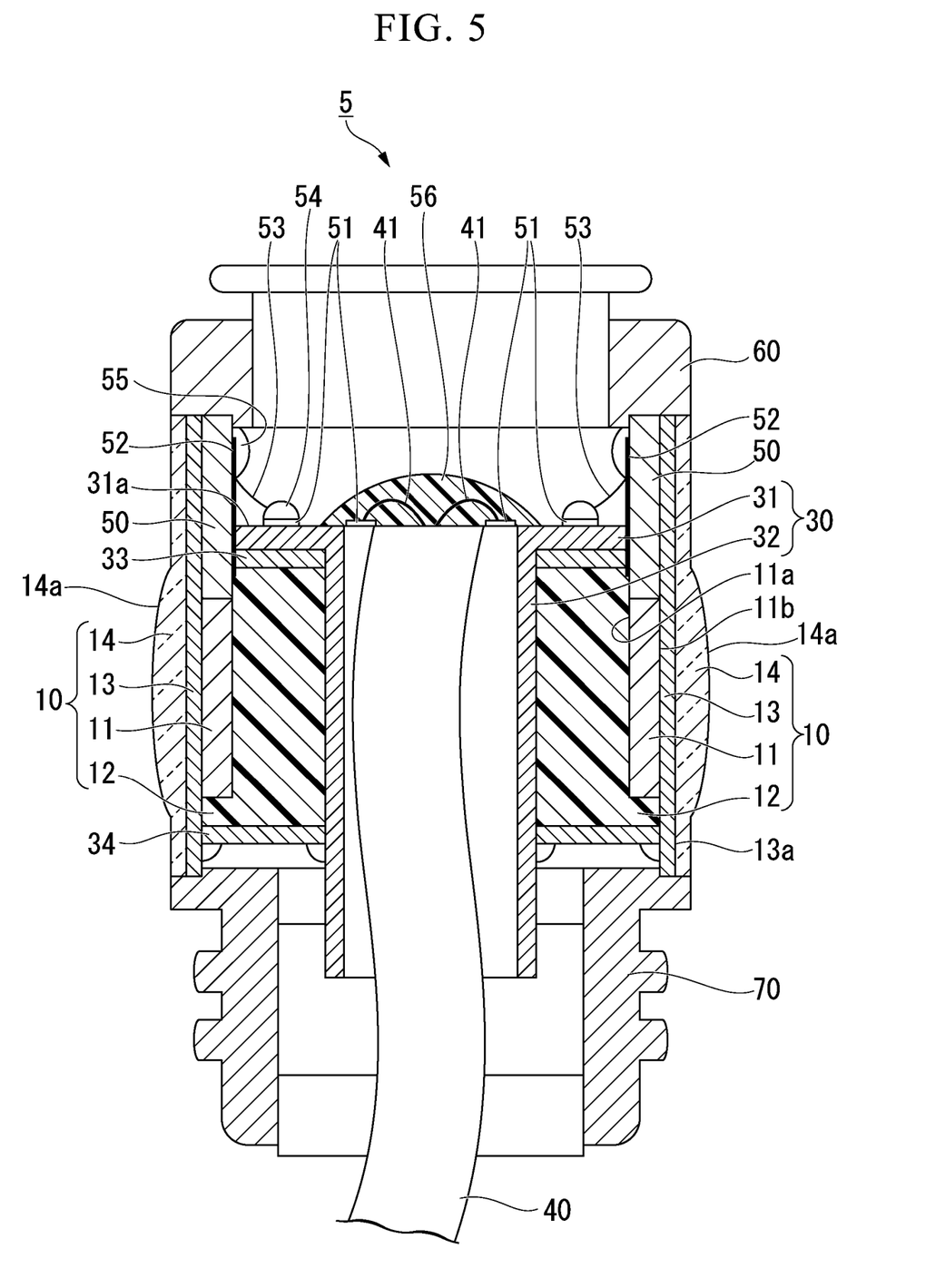
FIG. 5 is a schematic sectional view showing a constitution of primary parts of the ultrasonic endoscope of the second embodiment of the present invention.

FIG. 4 is a schematic front view showing a general constitution of an ultrasonic endoscope of a second embodiment of the present invention. FIG. 5 is a schematic sectional view showing a constitution of primary parts of the ultrasonic endoscope of the second embodiment of the present invention.

As shown in FIG. 4, an ultrasonic endoscope 1 of the present embodiment (an ultrasonic endoscope) includes an elongate insertion part 2 to be inserted into a body, a operation portion 3 connected to a proximal end of the insertion part 2, and a universal cord 4 extending from the operation portion 3.

The insertion part 2 is constructed in such a way that a rigid distal end portion 5, a bending portion 6, and a flexible tube portion 7 that is thin and long and has flexibility are connected in this order from the distal end thereof.

As shown in FIG. 5, the rigid distal end portion 5 includes a cylindrical member 30 and a plurality of ultrasonic transducers 10.

The cylindrical member 30 includes an annular flange 31 and a cylindrical portion 32 that extends from a central edge of the flange 31 in a direction of the flexible tube portion 7 (not shown) (a direction from above to below in FIG. 5).

A coaxial cable 40 is inserted into the cylindrical portion 32 of the cylindrical member 30.

Each ultrasonic transducer 10 is a device portion that emits ultrasonic waves to a subject. The plurality of ultrasonic transducers 10 are arranged along a circumferential surface of the cylindrical member 30 in a circumferential direction.

Each ultrasonic transducer 10 includes a piezoelectric element 11, a backing material 12, an acoustic matching layer 13, an acoustic lens 14, and an electrode (not shown).

The piezoelectric element 11 generates ultrasonic vibration when a voltage is applied by the electrode (not shown). The piezoelectric element 11 in the present embodiment is formed in a flat plate shape. One plate surface 11a of the piezoelectric element 11 is disposed at a position that faces the cylindrical portion 32 in a radial direction of the cylindrical member 30.

The backing material 12 is a member for absorbing the ultrasonic vibration from the plate surface 11a directed inside of the rigid distal end portion 5 in a radial direction among ultrasonic vibrations generated by the piezoelectric element 11. The backing material 12 fills a space between the cylindrical portion 32 and the piezoelectric element 11.

A resin material having a suitable vibration absorption characteristic is used as a material of the backing material 12.

The backing material 12 is sandwiched between annular members 33 and 34 into which the cylindrical portion 32 is inserted in an axial direction of the rigid distal end portion 5.

The annular member 33 is adjacent to the flange 31 and is attached to be in contact with a substrate 50 that extends from the piezoelectric element 11 in the distal end direction of the rigid distal end portion 5.

The annular member 34 is attached to be in contact with the acoustic matching layer 13 (to be described below) at a position nearer the flexible tube portion 7 (not shown) than the piezoelectric element 11.

The acoustic matching layer 13 is a layered part that reduces a difference in acoustic impedance between the subject and the piezoelectric element 11. Depending on the acoustic impedance of the subject, acoustic impedance of the acoustic matching layer 13 is suitably set, and thus reflection of ultrasonic waves at the subject is reduced.

The acoustic matching layer 13 is provided to cover at least the plate surface 11b which is the opposite side of the plate surface 11a of the piezoelectric element 11. For this reason, ultrasonic waves emitted from the plate surface 11b to the outside of the rigid distal end portion 5 in a radial direction via the acoustic matching layer 13 are efficiently introduced into the subject.

The acoustic matching layer 13 may be composed in a single layer or in multiple layers.

Each acoustic lens 14 converges ultrasonic waves that are generated by the piezoelectric element 11 and are propagated to the outside of the rigid distal end portion 5 in the radial direction through the acoustic matching layer 13, and emits the converged ultrasonic waves to the outside. The acoustic lens 14 is formed in a suitable shape for converging the ultrasonic waves. The acoustic lens 14 is provided to cover the acoustic matching layer 13 from the outside of the rigid distal end portion 5 in the radial direction.

The acoustic lens 14 has the same constitution as the acoustic lens 100 of the first embodiment, except that it is stacked on the acoustic matching layer 13, converges the ultrasonic waves generated by the piezoelectric element 11, and emits the ultrasonic waves from a lens surface 14a thereof.

In the flange 31 of the cylindrical member 30, a plurality of electrode pads 51 are provided on a surface 31a, which is an opposite side of the surface facing to the annular member 33.

Wirings 41 extending from the coaxial cable 40 are connected to the electrode pads 51. The electrode pads 51 and an electrode layer 52 provided on the substrate 50 are connected by wires 53.

The electrode pads 51 and the wires 53 are joined by solder 54. The electrode layer 52 and the wires 53 are joined by solder 55.

To prevent the wirings 41 from being disconnected from the electrode pads 51, for example, due to a load applied to the coaxial cable 40, connection portions between the electrode pads 51 and the wirings 41 are entirely covered with a potting resin 56.

A distal end structural member 60 is provided at the distal end of the rigid distal end portion 5 in order to seal the connection portions between the electrode pads 51 and the wirings 41. In addition, the rigid distal end portion 5 is connected to the bending portion 6 (not shown in FIG. 5) via a connecting member 70.

For example, the ultrasonic transducer 10 having the acoustic lens 14 of the present embodiment are manufactured as follows.

The piezoelectric element 11 in which the electrodes (not shown) are provided on the plate surfaces 11a and 11b and the acoustic matching layer 13 that is formed in advance are joined. Afterward, the substrate 50 is attached on the piezoelectric element 11 so as to extend in a surface direction. In addition, the annular members 33 and 34 are disposed at the prescribed positions.

Afterward, a resin composition for forming the backing material 12 is poured between the cylindrical member 30 and the piezoelectric element 11 surrounded by the annular members 33 and 34. When the resin composition is cured, the backing material 12 is formed.

Afterward, the acoustic lens 14 is formed on a surface 13a of the acoustic matching layer 13, the surface 13a is back side of the surface facing to the piezoelectric element 11. For example, the acoustic lens 14 is formed as follows depending on whether the orientation of the plate-like inorganic compound particles 100B is aligned or not.

In the case where the orientation is not aligned, a molding die of the acoustic lens 14 is disposed around the acoustic matching layer 13. A resin composition for forming the acoustic lens 14 is poured into the molding die. Before the resin composition is cured, the resin composition comes in contact with the acoustic matching layer 13 attached on the piezoelectric element 11. In this state, the resin composition is heat cured. Thus, the acoustic lens 14 joined to the acoustic matching layer 13 is formed.

In the case where the orientation is aligned along the lens surface 14a, the resin composition for forming the acoustic lens 14 is shaped into a sheet while being stretched by a roll. Furthermore, the stretched sheet is heat cured. Thus, the plate-like inorganic compound particles 100B are orientated in a surface direction of the sheet. The sheet is, for example, molded by punching or the like using a lens-shaped die by which the acoustic lens 14 is formed. The acoustic matching layer 13 and the acoustic lens 14 manufactured in this way are adhered to each other using an adhesive whose acoustic impedance is adjusted to a value between the acoustic impedances of the acoustic matching layer 13 and the acoustic lens 14.

In this way, the ultrasonic transducer 10 is manufactured.

Since the acoustic lens 14 of the present embodiment has the same constitution as the acoustic lens 100 of the first embodiment, it has the same action as the acoustic lens 100. For this reason, according to the acoustic lens 14, the excellent acoustic characteristics are provided, and the durability against physical contact is improved.

According to the ultrasonic endoscope 1 of the present embodiment, since the ultrasonic transducer 10 includes the acoustic lens 14, excellent observation of an ultrasonic image becomes possible, and the durability against physical contact is improved.

[Modification]

Next, an ultrasonic endoscope acoustic lens of a modification of the second embodiment will be described.

Figure 6:
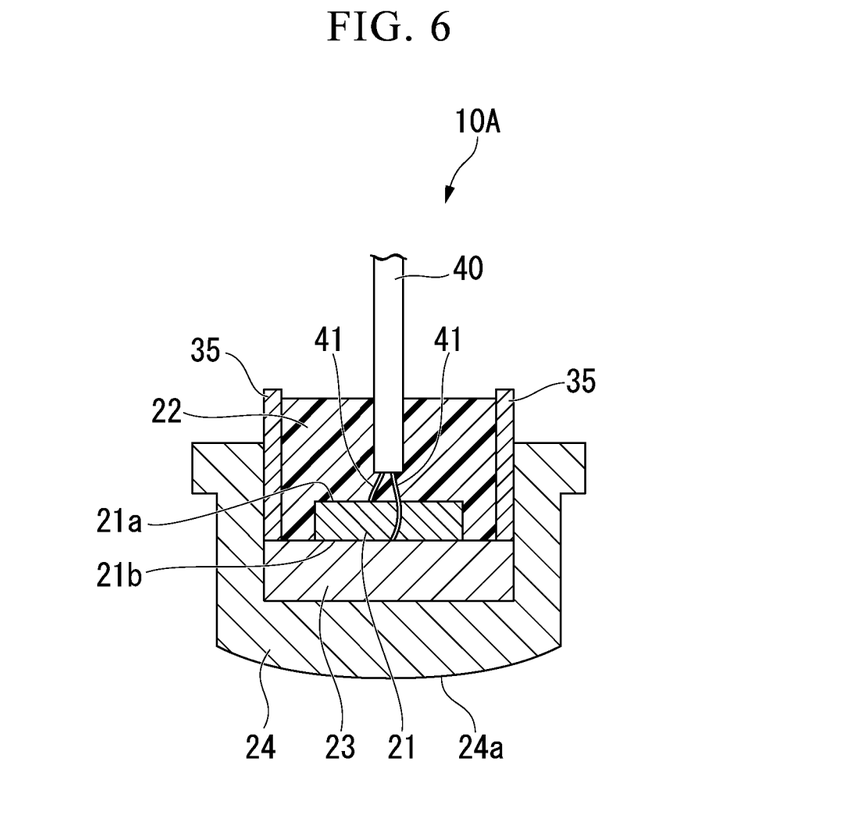
FIG. 6 is a schematic sectional view showing a modification of the ultrasonic endoscope acoustic lens that can be used in the ultrasonic endoscope of the second embodiment of the present invention.

FIG. 6 is a schematic sectional view showing a modification of an ultrasonic endoscope acoustic lens that can be used in the ultrasonic endoscope of the second embodiment of the present invention.

An ultrasonic transducer 10A shown in FIG. 6 is a modification of the ultrasonic transducer 10 in the second embodiment. The ultrasonic transducer 10A may be substituted with the ultrasonic transducer 10 in the ultrasonic endoscope 1 of the second embodiment.

The ultrasonic transducer 10A includes a piezoelectric element 21, a backing material 22, an acoustic matching layer 23, and an acoustic lens 24 of this modification (an ultrasonic endoscope acoustic lens) instead of the piezoelectric element 11, the backing material 12, the acoustic matching layer 13, and the acoustic lens 14 of the ultrasonic transducer 10.

Hereinafter, the difference from the second embodiment is mainly described.

The piezoelectric element 21 has a disc shape. Electrodes (not shown) for applying a voltage to the piezoelectric element 21 are provided on both surfaces 21a and 21b of the piezoelectric element 21. Wirings 41 extending from a coaxial cable 40 are connected to the electrodes (not shown).

The backing material 22 is provided to cover one surface 21a and a lateral surface of the piezoelectric element 21 in a state where a distal end of the coaxial cable 40 and the wirings 41 are included therein.

The same material as the backing material 12 of the second embodiment may be adopted as a material of the backing material 22.

The acoustic matching layer 23 is formed of a disc having a larger diameter than the piezoelectric element 21. The acoustic matching layer 23 is provided to be in contact with the other surface 21b of the piezoelectric element 21. A cylindrical member 35 having the same outer diameter as the acoustic matching layer 23 is vertically provided on an outer circumferential portion of a surface of the acoustic matching layer 23 which is in contact with the piezoelectric element 21. An inner circumferential surface of the cylindrical member 35 is in close contact with the lateral surface of the backing material 22.

The same material as the acoustic matching layer 13 of the second embodiment may be adopted as a material of the acoustic matching layer 23.

The acoustic lens 24 includes a circular lens area in a plan view, this shape corresponds to the disc shapes of the piezoelectric element 21 and the acoustic matching layer 23. However, the acoustic lens 24 is formed in the shape of a cap that covers a part of a lateral surface of the acoustic matching layer 23 and a part of a lateral surface of the cylindrical member 35.

The acoustic lens 24 has the same constitution as the acoustic lens 14 of the second embodiment except that an entire shape including the lens surface 24a differs.

In order to manufacture the ultrasonic transducer 10A, the acoustic matching layer 23 is first joined to the surface 21b of the piezoelectric element 21. Afterward, a resin composition for forming the backing material 22 is poured into a space surrounded by the acoustic matching layer 23 and the cylindrical member 35 that is vertically provided on the outer circumferential portion of the acoustic matching layer 23, and is cured, and thereby the backing material 22 is molded.

Afterward, the acoustic lens 24 is formed so as to cover outer surfaces (lateral surfaces) of the acoustic matching layer 23 and the cylindrical member 35, and thereby the ultrasonic transducer 10A is manufactured.

The acoustic lens 24 of this modification is only different in shape from the acoustic lens 14 of the second embodiment, and thus has the same action as in the second embodiment.

In the description of each embodiment and the modification, the case where the ultrasonic endoscope acoustic lens is used in the ultrasonic endoscope has been described by way of example. However, the ultrasonic endoscope acoustic lens may be used in various medical devices that use ultrasonic waves or devices other than the medical devices.

EXAMPLES

Hereinafter, Examples 1 to 15 relevant to materials for manufacturing the ultrasonic endoscope acoustic lenses of the embodiments and the modification will be described along with Comparative Examples 1 and 2.

The examples were formed of test samples molded out of materials for forming the acoustic lenses 100, 14 and 24. The comparative examples were formed of test samples molded out of materials for forming acoustic lenses thereof.

All the test samples were each shaped of a rectangular plate of 40 mm length×40 mm width×0.4 mm height.

For all base materials of the test samples, the same diorganopolysiloxane was used.

Characteristics and results of evaluation of inorganic compound particles used in the test samples of Examples 1 to 15 and Comparative Examples 1 and 2 are shown in Table 1 below.

TABLE 1

| | Inorganic compound particles | Added amount (parts by mass) | Surface-direction average particle size (nm) | Aspect ratio | Gradient (°) | Results of evaluation | | |
|---|---|---|---|---|---|---|---|---|
| | | | | | | Pinhole resistance | Acoustic IMP | Comprehensive |
| Example 1 | Plate-like alumina | 0.5 | 1000 | 100 | 0 | C | B | B |
| Example 2 | Plate-like alumina | 5 | 1000 | 100 | 0 | A | B | A |
| Example 3 | Plate-like alumina | 30 | 1000 | 100 | 0 | A | A | A |
| Example 4 | Plate-like alumina | 90 | 1000 | 100 | 0 | A | B | A |
| Example 5 | Plate-like alumina | 150 | 1000 | 100 | 0 | B | C | B |
| Example 6 | Plate like alumina | 30 | 5 | 100 | 0 | C | B | B |
| Example 7 | Plate-like alumina | 30 | 20 | 100 | 0 | B | B | B |
| Example 8 | Plate-like alumina | 30 | 20000 | 100 | 0 | A | B | A |
| Example 9 | Plate-like alumina | 30 | 50000 | 100 | 0 | C | B | B |
| Example 10 | Plate-like alumina | 30 | 1000 | 1 | 0 | C | B | B |
| Example 11 | Plate-like alumina | 30 | 1000 | 5 | 0 | B | B | B |
| Example 12 | Plate-like alumina | 30 | 1000 | 1500 | 0 | B | B | B |
| Example 13 | Plate-like alumina | 30 | 1000 | 3000 | 0 | C | B | B |
| Example 14 | Plate-like alumina | 30 | 1000 | 100 | 30 | B | B | B |
| Example 15 | Plate-like alumina | 30 | 1000 | 100 | 60 | C | B | B |
| Comparative Example 1 | — | — | — | — | — | D | C | D |
| Comparative Example 2 | Coarse alumina | 100 | 500 | — | — | C | C | D |

As shown in Table 1, in the test samples of Examples 1 to 15, plate-like alumina was used as the inorganic compound particles. However, added amounts, surface-direction average particle sizes, and aspect ratios of the inorganic compound particles were different.

Example 1

In a test sample of Example 1, plate-like alumina having a surface-direction average particle size of 1000 nm±100 nm and an aspect ratio of 100±10 was used as inorganic compound particles.

In Table 1, for brevity, the surface-direction average particle size and the aspect ratio are simply marked with "1000 nm" and "100." Similarly, in the surface-direction average particle sizes and the aspect ratios of the other examples in Table 1, when values thereof in the table are defined as X and Y, the surface-direction average particle size is X±0.1X, and the aspect ratio is Y±0.1Y.

An added amount of the plate-like alumina in Example 1 was set to 0.5 parts by mass with respect to 100 parts by mass of a base material.

The test sample of Example 1 was manufactured as follows. A resin composition before curing was formed by kneading a base material and inorganic compound particles. Afterward, the resin composition was roll-pressed by three heated mill rolls such that an orientated state of the plate-like alumina is arranged. Thus, the resin composition was molded in the shape of a sheet having a thickness of 0.4 mm, and was cured. Afterward, a molded product was cut into a size of 40 mm×40 mm in a plan view, and thereby the test sample of Example 1 was obtained.

This manufacturing method was also used in Examples 2 to 13 (to be described below).

Examples 2 to 5

Test samples of Examples 2 to 5 were different in added amount of plate-like alumina from the test sample of Example 1. The added amount of the plate-like alumina in Examples 2 to 5 was set to 5 parts by mass, 30 parts by mass, 90 parts by mass, and 150 parts by mass.

Examples 6 to 9

In Example 6, in place of the plate-like alumina in Example 1, plate-like alumina having a surface-direction average particle size of 5 nm±0.5 nm (marked with "5 nm" in Table 1) and an aspect ratio 100±10 (marked with "100" in Table 1) was used. An added amount of the plate-like alumina in Example 6 was set to 30 parts by mass with respect to 100 parts by mass of a base material.

The plate-like alumina used in test samples of Examples 7 to 9 was different in surface-direction average particle size from the plate-like alumina of the test sample of Example 6. The surface-direction average particle sizes of the plate-like alumina in Examples 7 to 9 was set to 20 nm±2 nm (marked with "20 nm" in Table 1), 20000 nm±2000 nm (marked with "20000 nm" in Table 1), and 50000 nm±5000 nm (marked with "50000 nm" in Table 1).

Examples 10 to 13

Plate-like alumina used in test samples of Examples 10 to 13 was different in aspect ratio from the plate-like alumina of the test sample of Example 3. The aspect ratio of the plate-like alumina in Examples 10 to 13 was set to 1±0.1 (marked with "1" in Table 1), 5±0.5 (marked with "5" in Table 1), 1500±150 (marked with "1500" in Table 1), and 3000±300 (marked with "3000" in Table 1).

Examples 14 and 15

Test samples of Examples 14 and 15 were the same in constitution and added amount of the plate-like inorganic compound particles 100B as that of Example 3, and were different in method of manufacturing a test sample from that of Example 3.

The test samples of Examples 14 and 15 were molded such that an orientated state of the plate-like alumina having the same resin composition as in Example 3 varied like the case where the aforementioned orientated state is not arranged.

As the test samples of Examples 14 and 15, two samples that are different in magnitude of a gradient of orientation were selected from several molded test samples.

Comparative Examples 1 and 2

A test sample of Comparative Example 1 was formed of a base material only. The test sample of Comparative Example 1 corresponded to the case where the added amount of the plate-like alumina in Example 1 above was set to 0 parts by mass.

In a test sample of Comparative Example 2, in place of the plate-like alumina of Example 1 above, coarse alumina having an average particle size of about 500 nm±50 nm was used as inorganic compound particles. In Table 1, for brevity, the average particle size is listed in the column "surface-direction average particle size."

The average particle size of the coarse alumina was measured by the same measuring instrument used for the surface-direction average particle size.

The test samples of Comparative Examples 1 and 2 were manufactured in the same way as in Example 1 above except that resin compositions thereof were different from that of Example 1.

[Evaluating Method]

As evaluations of the test samples, evaluation of gradients of the plate-like inorganic compound particles (only Examples 1 to 15), evaluation of pinhole resistance, evaluation of acoustic impedance (marked with "acoustic IMP" in Table 1), and comparative evaluation were performed.

In the gradient evaluation, as set forth in the first embodiment, first and second sections were formed, and a gradient was estimated from a value of gradient distribution from an electron microscopic image of each section.

In numerical values of the gradients listed in Table 1, rates per class of a width of 5° (more than or equal to Z° and less than Z°+5°) were obtained as β1(Z) and β2(Z) from distribution of the gradients in the first and second sections described in the first embodiment, and a representative value Z of a class in which β1(Z)×β2(Z) was maximized was marked.

In the pinhole resistance evaluation, a pinhole test for allowing a test weight to freely fall from an upper portion of each test sample was performed. As the test weight, an iron weight having a tip radius of 0.75 mm and a mass of 50 g was used. The test weight freely fell from a position having a height of 90 mm toward the test sample.

In the evaluation, a state of the test sample after testing was visually observed, and was determined to be four grades of "very good" (A in Table 1), "good" (B in Table 1), "fair" (C in Table 1), and "no good" (D in Table 1).

In a case where no hole was open, and no dent and crack occurred, this was determined to be "very good." In a case where no hole was open but a dent occurred, this was determined to be "good." In a case where no hole was open but a crack occurred on a surface, this was determined to be "fair." In a case where a hole was open, this was determined to be "no good."

The acoustic impedance was calculated by measuring a density and a speed of sound of the test sample.

In the acoustic impedance evaluation, the acoustic impedance was determined to be four grades of "very good" (A in Table 1), "good" (B in Table 1), "fair" (C in Table 1), and "no good" (D in Table 1). The closer an acoustic impedance to that of a human body (1.4) was, the higher the evaluation it got.

To be specific, in a case where the acoustic impedance was 1.2 or more and 1.6 or less, this was determined to be "very good." In a case where the acoustic impedance was more than or equal to 1.0 and less than 1.2, or more than 1.6 and less than or equal to 1.8, this was determined to be "good." In a case where the acoustic impedance was more than or equal to 0.8 and less than 1.0, or more than 1.8 and less than or equal to 2.0, this was determined to be "fair." In a case where the acoustic impedance was less than 0.8 or more than 2.0, this was determined to be "no good."

The comprehensive evaluation was performed by a combination of the pinhole resistance evaluation and the acoustic impedance evaluation. Hereinafter, the results of each evaluation were represented by arranging signs in the order of the pinhole resistance evaluation and the acoustic impedance evaluation.

In a case of (A, A), (A, B), and (B, A), the comprehensive evaluation was determined to be "very good" (A in Table 1).

In a case of (B, B), (B, C), and (C. B), the comprehensive evaluation was determined to be "good" (B in Table 1).

In a case of (C, C), (C, D), (D, C), and (D, D), the comprehensive evaluation was determined to be "no good" (D in Table 1).

[Results of Evaluation]

As shown in Table 1, the gradient of the plate-like inorganic compound particle was "0°" in Examples 1 to 13, and "30°" and "60°" in Examples 14 and 15.

The pinhole resistance evaluation was determined that Examples 2, 3, 4 and 8 were "very good," that Example 5, 7, 11, 12 and 14 were "good," that Example 1, 6, 9, 10, 13 and 15 and Comparative Example 2 were "fair," and that Comparative Example 1 was "no good."

In Comparative Example 1, since the inorganic compound particles were not added, it was conceivable that a strength became insufficient and a hole was open. In contrast, in a case where the inorganic compound particles were added, since a mechanical strength of any test sample was improved, it was conceivable that pinhole resistance was improved.

However, the degree of the improvement was different according to conditions of the inorganic compound particles. For example, in a case where the inorganic compound particles were not plate-like (Comparative Example 2), in a case where the added amount was small (Example 1), in a case where the surface-direction average particle size was too small or large (Examples 6 and 9), and in a case where the aspect ratio was too small or large (Examples 10 and 13), they were "fair." As could be seen from Examples 3, 14 and 15, as the gradients of the plate-like inorganic compound particles became close to 0°, the pinhole resistance was better.

The acoustic impedance evaluation was determined that Example 3 was "very good," that Example 5 and Comparative Examples 1 and 2 were "fair," and that the examples other than Examples 3 and 5 were "good."

The comprehensive evaluation was determined from the above results that Examples 2, 3, 4 and 8 were "very good," that the other examples was "good," and that Comparative Examples 1 and 2 were "no good."

While the preferred embodiments, the modification, and the examples of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. An ultrasonic endoscope acoustic lens comprising:
a base material composed of a diorganopolysiloxane or a silicone rubber compound utilizing a diorganopolysiloxane as a main component; and
inorganic compound particles having plate-like shapes and dispersed in the base material,
wherein the ultrasonic endoscope acoustic lens has a convex surface, and
wherein at least 49% of the inorganic compound particles have gradients with respect to the convex surface of 0° or more and 45° or less.

2. The ultrasonic endoscope acoustic lens according to claim 1, wherein an average particle size of the inorganic compound particles in a surface direction is 10 nm or more and 30 μm or less.

3. The ultrasonic endoscope acoustic lens according to claim 1, wherein an aspect ratio of the inorganic compound particles which is a ratio of an average particle size in a surface direction to a thickness is 2 or more and 2000 or less.

4. The ultrasonic endoscope acoustic lens according to claim 1, wherein the inorganic compound particles contain one or more materials selected from the group consisting of alumina, silica, boehmite, cerium oxide, titanium oxide, magnesium oxide, zinc oxide, boron nitride, aluminum nitride, and aluminum hydroxide.

5. The ultrasonic endoscope acoustic lens according to claim 1, wherein 1 part by mass or more and 100 parts by mass or less of the inorganic compound particles are included with respect to 100 parts by mass of the base material.

6. An ultrasonic endoscope having the ultrasonic endoscope acoustic lens according to claim 1.

* * * * *